United States Patent [19]

Vollbrecht

[11] Patent Number: 4,533,733

[45] Date of Patent: Aug. 6, 1985

[54] PROCESS FOR OBTAINING CYANURIC CHLORIDE IN SOLID OR LIQUID FORM

[75] Inventor: Heinz-Rüdiger Vollbrecht, Stein, Fed. Rep. of Germany

[73] Assignee: SKW Trostberg Aktiengesellschaft, Trostberg, Fed. Rep. of Germany

[21] Appl. No.: 636,334

[22] Filed: Jul. 31, 1984

[30] Foreign Application Priority Data

Oct. 11, 1983 [DE] Fed. Rep. of Germany ....... 3336994

[51] Int. Cl.³ .......................................... C07D 251/28
[52] U.S. Cl. ..................................... 544/190; 544/191
[58] Field of Search ............................... 544/190, 191

[56] References Cited

U.S. PATENT DOCUMENTS

| | | | |
|---|---|---|---|
| 2,734,058 | 2/1956 | Schulz et al. | 544/190 |
| 2,742,977 | 4/1956 | Williams et al. | 544/190 |
| 2,753,346 | 7/1956 | Huemer | 544/190 |
| 3,409,619 | 11/1968 | Kosel | 544/190 |
| 3,539,565 | 11/1970 | Evers et al. | 544/190 |

Primary Examiner—John M. Ford
Attorney, Agent, or Firm—Felfe & Lynch

[57] ABSTRACT

The present invention provides a process for obtaining cyanuric chloride in solid and/or liquid form from an optionally contaminated cyanuric chloride vapor, wherein cyanuric chloride, after dilution with an air stream with a temperature of from 60° to 140° C., is introduced into the lower part of a separation chamber cooled to a temperature of from 20° to 50° C., the separated solid cyanuric chloride is optionally converted into liquid form in a melt container at a temperature above 146° C. and the cyanuric chloride vapor, after again diluting with hot air with a temperature of from 50° to 140° C., returned from the melt container into the separation chamber, whereas the cyanuric chloride-free waste gases are withdrawn above the desublimation zone of the separation chamber.

10 Claims, 2 Drawing Figures

PROCESS FOR OBTAINING CYANURIC CHLORIDE IN SOLID OR LIQUID FORM

The present invention is concerned with a process for obtaining cyanuric chloride in solid or liquid form.

Cyanuric chloride is an important technical intermediate product in the production of plant protection agents, dyestuffs, optical brightener and pharmaceuticals, as well as of textile and rubber adjuvants. After the trimerisation of cyanogen chloride with the help of catalysts, it is obtained in gaseous form, it thereby being present essentially as a mixture with excess cyanogen chloride and chlorine. This gas mixture was usually passed to separation chambers, it thereby being converted into the solid form on cooled wall surfaces. A disadvantage of this desublimation is that the cyanuric chloride is deposited in the form of coarse crystals on the walls and removal devices, which resulted in considerable technical difficulties, quite apart from the poor quality of the product thereby obtained. For overcoming this problem, the attempt has been made, according to Federal Republic of Germany Patent Specification No. 12 66 308, to spray the cyanuric chloride with a readily evaporating inert cooling liquid, for example chloroform, by means of an atomising nozzle. In this way, finely divided cyanuric chloride is admittedly obtained but, in the case of this process, blockages of the nozzle readily occur. Furthermore, recovery of the cooling medium was technically not easy.

Because of the difficult handling of solid cyanuric chloride, in those cases in which a quick use of the cyanuric chloride takes place, it is desirable to obtain the cyanuric chloride in liquid form.

From Federal Republic of Germany Pastent Specification No. 23 32 636, it is known to condense gaseous cyanuric chloride with an adjuvant liquid in a fractionation column. However, it is hereby disadvantageous that a great technical expense is necessary for working up the adjuvant liquid, as well as for the purification of the waste gases.

Finally, in Federal Republic of Germany Patent Specification Nos. 28 43 381 and 28 43 383, there is described a process according to which, as desired, liquid or solid cyanuric chloride can be produced, which process is characterized in that the gaseous reaction mixture is passed into an apparatus combination comprising a separation column and condenser and, by temperature control at the outlet of the condenser, the cyanuric chloride is partly condensed in the column, whereas gaseous cyanuric chloride, which emerges at the head of the column, is obtained as a solid material in conventional separation chambers. Because of the laborious combination of apparatus, this process also requires high investment and operational costs and thus does not represent an optimum solution of the problem.

Therefore, it is an object of the present invention to provide a process for obtaining cyanuric chloride in solid and/or liquid form which does not display the above-mentioned disadvantages and, with technically simple means, enables cyanuric chloride to be obtained, as desired, in liquid or solid form or in both forms and which, with regard to purity and particle distribution of the solid material, also provides good results.

Thus, according to the present invention, there is provided a process for obtaining cyanuric chloride in solid and/or liquid form from an optionally contaminated cyanuric chloride vapour, wherein cyanuric chloride, after dilution with an air stream with a temperature of from 60° to 140° C., is introduced into the lower part of a separation chamber cooled to a temperature of from 20° to 50° C., the separated solid cyanuric chloride is optionally converted into liquid form in a melt container at a temperature above 146° C. and the cyanuric chloride vapour, after again diluting with hot air with a temperature of from 60° to 140° C., returned from the melt container into the separation chamber, whereas the cyanuric chloride-free waste gases are withdrawn above the desublimation zone of the separation chamber.

We have, surprisingly, found that even without the help of a column, cyanuric chloride with a high degree of purity can be obtained, as desired, in liquid or solid form, the solid cyanuric chloride thereby also being characterised by an especially finely divided particle spectrum. It was not to have been foreseen that this process could be carried out technically without any problems, for example without plugging.

In the case of the process according to the present invention, the cyanuric chloride vapour, which can still contain numerous impurities, for example cyanogen chloride or chlorine, is diluted with an air stream with a temperature of from 60° to 140° C. and especially of from 100° to 120° C., and subsequently passed into conventional separation chambers. The amount of air stream is preferably from 250 to 750 liters/kg. gaseous cyanuric chloride, an amount of from 400 to 500 liters/kg. of cyanuric chloride having proved to be especially advantageous. By means of the dilution of the cyanuric chloride according to the present invention, it can be achieved that the cyanuric chloride does not condense in the pipes and lead to undesired plugging.

Furthermore, upon introducing the cyanuric chloride into the separation chamber, turbulence formation prevents coarse crystals already in the upper part of the separation chamber from depositing on the walls. On the contrary, desublimation of solid cyanuric chloride takes place in the lower part of the separation chamber, which has a cooling temperature of from 20° to 50° C. and especially of from 30° to 40° C. In this way, a good purification and an excellent particle distribution of the solid product can be achieved. The waste gases, together with the air stream, are withdrawn above the desublimation zone, the solid cyanuric chloride is removed and, according to requirements, introduced wholly or partly into a melting container at a temperature above 146° C. in order to convert the cyanuric chloride into liquid form. The cycle is closed in that the cyanuric chloride which is gaseous at the melting temperature used, which can still contain traces of impurities, together with the hot air stream at a temperature of from 60° to 140° C., is returned to the separation chamber. The choice of the melting temperature has an important influence of the purity of the cyanuric chloride because the higher this temperature the more gaseous cyanuric chloride is circulated and the better is the purification yield because the waste gases are continuously removed from the separation chamber. The process according to the present invention makes possible not only the selective obtaining of solid or liquid cyanuric chloride but also represents a purification process, in the case of which it is not essential to start from gaseous cyanuric chloride. In one embodiment of the process according to the present invention, solid cyanuric chloride can also be melted. The vaporised cyanuric chloride can be cycled until it displays the necessary degree of purity.

To maintain the melting temperature, it is, from the energy point of view, especially favourable to utilise the heat given off, for example the heat obtained in the case of the trimerisation of the cyanogen chloride and/or of the deposition of the cyanuric chloride.

The process according to the present invention will now be described in more detail with reference to FIGS. 1 and 2 of the accompanying drawings and to the following Examples 1 and 2.

DESCRIPTION OF THE INVENTION

Figure 1:
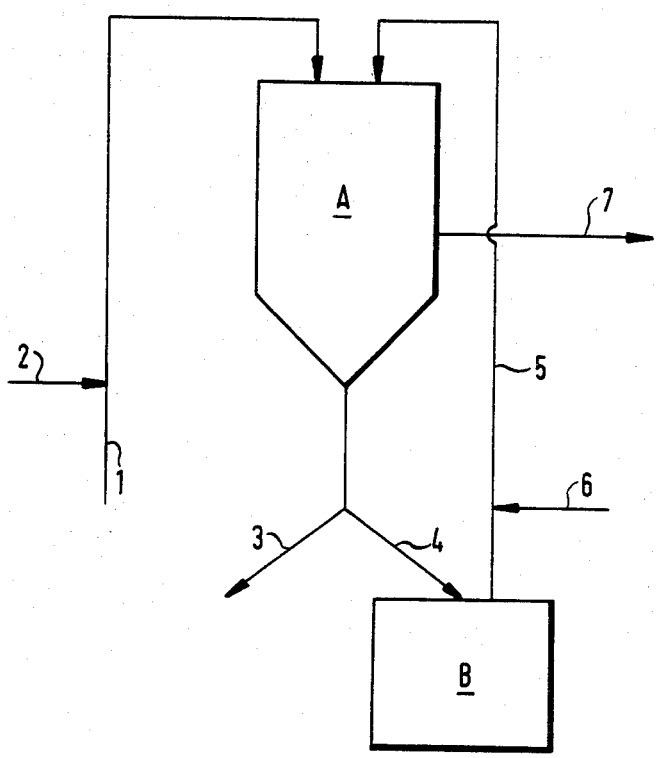
FIG. 1 shows schematically the method of obtaining solid or liquid cyanuric chloride from cyanuric chloride vapour, such as is obtained, for example, after the trimerisation of cyanogen chloride.

Referring to FIG. 1, cyanuric chloride vapour is passed through pipe 1 to a separation chamber A after an air stream has been dosed in via pipe 2. After desublimation, solid material is removed via pipe 3 or is passed via pipe 4 into a melt container B. The return of the cyanuric chloride vapour from the melt container B into the separation chamber A takes place after dilution with the air introduced from 6 via pipe 5, whereas waste gases from the separation chamber are withdrawn via pipe 7.

Figure 2:
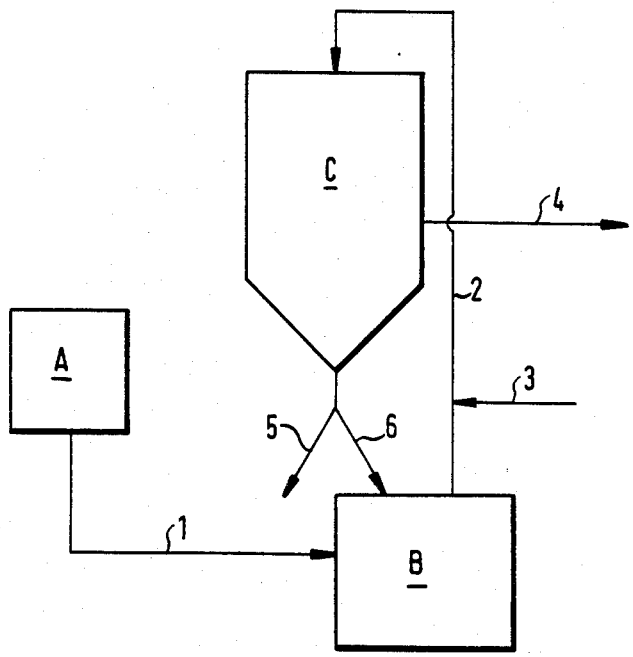
FIG. 2 shows a block diagram for the purification of solid cyanuric chloride following the invention.

Referring to FIG. 2, from a storage container A, solid cyanuric chloride is passed via a pipe 1 into a melt container B, which is connected by pipe 2 with a separation chamber C. After dilution with an air stream from pipe 3, the cyanuric chloride vapour passes through pipe 2 into C and is there deposited out as solid material, whereas the waste gases leave the separation chamber C via pipe 4. The removal of the solid cyanuric chloride takes place via pipe 5 and the return of the solid material into the melt container via pipe 6.

EXAMPLE 1.

200 kg. cyanuric chloride with a temperature of 170° C., after dilution thereof with 90 kg. of hot air at 100° C., are passed hourly into the separation chamber, the lower part of which has a temperature of 30° C. After desublimation, 150 kg. solid cyanuric chloride are removed and the remaining 50 kg. are melted and continuously withdrawn. The cyanuric chloride gas obtained corresponding to the vapour pressure of the cyanuric chloride at the melting temperature is diluted with 20 kg. of air and again returned to the separation chamber.

The analysis of the product obtained in this manner gives the following composition:

| | |
|---|---|
| cyanuric chloride | >99.5% |
| triazine polymer | <0.1% |
| hydroxytriazine | <0.5% |

The particle spectrum of the solid cyanuric chloride has the following composition:

| | |
|---|---|
| >250 μm. | 0.8% |
| 125–250 μm. | 2.5% |
| 63–125 μm. | 2.3% |
| 40–63 μm. | 13.9% |
| <40 μm. | 80.5% |

EXAMPLE 2.

100 kg. of solid cyanuric chloride with the following composition:

| | |
|---|---|
| cyanuric chloride | 98.53% |
| triazine polymer | 0.57% |
| hydroxytriazine | 0.90% | are introduced from a storage container into the melt container which is operated at a temperature of 190° C. and is connected with the separation chamber. Before entry into the separation chamber, the cyanuric chloride vapour is diluted with 20 kg. of air which has a temperature of 100° C. The product is deposited and removed continuously. It has the following analysis:

| | |
|---|---|
| cyanuric chloride | >99.5% |
| triazine polymer | <0.1% |
| hydroxytriazine | <0.5% |

The particle spectrum of the product corresponds to that of Example 1.

I claim:

1. Process for recovering cyanuric chloride from cyanuric chloride containing vapor, comprising the steps of diluting the cyanuric chloride containing vapor, with a hot air stream having a temperature of from 60° to 140° C., and
    introducing the diluted vapor into the lower part of a separation chamber cooled to a temperature of from 20° to 50° C. to precipitate the cyanuric chloride from the vapor.

2. Process according to claim 1, wherein the temperature of the hot air stream is from 100° to 120° C.

3. Process according to claim 1 wherein the lower part of the separation chamber has a temperature of from 30° to 40° C.

4. Pocess according to claim 1, wherein 250 to 750 liters of the hot air are added to the cyanuric chloride per kg. thereof.

5. Process according to claim 4, wherein 400 to 500 liters of air are added to the cyanuric chloride per kg. thereof.

6. Process according to claim 1 further comprising introducing into the cyanuric chloride melt present in the melt container, impure solid cyanuric chloride.

7. Process according to claim 1 wherein the cyanuric chloride containing vapor is generated by trimerization of cyanogen chloride and, for the maintenance of the melt temperature, there is utilized the waste heat obtained by the trimerization of the cyanogen chloride and/or by the desublimation of the cyanuric chloride.

8. Process according to claim 1 further comprising
    separating the precipitated cyanuric chloride from the vapor,
    heating the cyanuric chloride in a melt container to form a melt above 146° C.;
    diluting vapors formed above the cyanuric chloride melt with hot air with a temperature of from 60° to 140° C.; and
    removing the diluted vapors from the melt continer, to leave purified molten cyanuric chloride in the melt container for recovery.

9. The process of claim 8 wherein the hot air from the melt container is passed into the separation chamber for precipitation of cyanuric chloride therefrom.

10. The process of claim 8 wherein the hot air stream diluting the cyanuric chloride containing vapor comprises the hot air from the melt container.

* * * * *

UNITED STATES PATENT AND TRADEMARK OFFICE
CERTIFICATE OF CORRECTION

PATENT NO. : 4,533,733
DATED : August 6, 1985
INVENTOR(S) : Heinz-Rüdiger Vollbrecht It is certified that error appears in the above-identified patent and that said Letters Patent is hereby corrected as shown below:

Claim 6, line 1, "1" should be -- 8 --.

Signed and Sealed this

Eighteenth Day of March 1986

[SEAL]

Attest:

DONALD J. QUIGG

Attesting Officer

Commissioner of Patents and Trademarks